United States Patent
Osajima et al.

(10) Patent No.: US 6,616,849 B1
(45) Date of Patent: Sep. 9, 2003

(54) METHOD OF AND SYSTEM FOR CONTINUOUSLY PROCESSING LIQUID MATERIALS, AND THE PRODUCT PROCESSED THEREBY

(75) Inventors: Yutaka Osajima, Hiroshima-ken (JP); Mitsuya Shimoda, Fukuoka-ken (JP); Michinosuke Takada, Kyoto-fu (JP); Masaki Miyake, Kyoto-fu (JP)

(73) Assignee: Shimadzu Corporation, Kyoto (JP)

(*) Notice: Subject to any disclaimer, the term of this patent is extended or adjusted under 35 U.S.C. 154(b) by 0 days.

(21) Appl. No.: 09/562,189

(22) Filed: May 2, 2000

(30) Foreign Application Priority Data

Aug. 25, 1999 (JP) .......................................... 11-238192

(51) Int. Cl.⁷ ................................................. C02F 1/20
(52) U.S. Cl. ...................... 210/750; 210/764; 210/188; 210/192; 210/199; 210/205; 210/252
(58) Field of Search ................................. 210/750, 764, 210/188, 192, 198.1, 199, 205, 252

(56) References Cited

U.S. PATENT DOCUMENTS 3,966,981 A * 6/1976 Schultz
5,514,264 A * 5/1996 Shane
5,520,943 A * 5/1996 Osajima et al.
5,704,276 A * 1/1998 Osajima et al.

* cited by examiner

Primary Examiner—Betsey Morrison Hoey
(74) Attorney, Agent, or Firm—Armstrong, Westerman & Hattori, LLP

(57) ABSTRACT

The present invention proposes a method of and system for continuously processing liquid material by which enzymes in the liquid material are inactivated and the liquid material is sterilized effectively. In one example of the system according to the present invention, a liquid material is introduced into a processing chamber 11 from an introduction port at the bottom, and liquefied carbon dioxide formed into micro-particles by a filter 16 is also introduced in the chamber 11. The micro-particles of liquefied carbon dioxide dissolves into the liquid material efficiently. The liquid material taken out from a take-out port 18 is introduced into a warming pipe 20 kept at such a preset temperature and pressure where the carbon dioxide turns to a supercritical fluid. After that, the liquid material is introduced through a pressure control valve 24 into a pressure-reducing chamber 24. The carbon dioxide rapidly changes from supercritical fluid to gas, and vaporizes from the liquid material. The step of dissolving carbon dioxide into the liquid material and the step of processing the liquid material with the supercritical fluid are carried out independently under respective optimized temperature-and-pressure condition. Therefore, the processing time can be shortened even with a small-sized processing chamber 11, and there is no need to pre-heat the liquid material.

14 Claims, 6 Drawing Sheets

Fig. 2

| SEPCIES | ENZYMES REMAINING ACTIVE (%) | | |
| --- | --- | --- | --- |
| | PRESENT CASE | REFERENCE CASE 1 | REFERENCE CASE 2 |
| PECTINESTERASE | 8.0 | 9.2 | 12.4 |
| GLUCOAMYLASE | 13.5 | 12.1 | 14.7 |
| ACID PROTEASE | 7.8 | 9.3 | 12.7 |
| CARBOXYPEPTIDASE | 3.7 | 4.2 | 4.9 |
| LIPASE | 2.4 | 3.3 | 5.9 |
| $\alpha$-AMYLASE | 6.1 | 5.6 | 8.5 |
| $\beta$-AMYLASE | 4.9 | 4.4 | 7.7 |

METHOD OF AND SYSTEM FOR CONTINUOUSLY PROCESSING LIQUID MATERIALS, AND THE PRODUCT PROCESSED THEREBY

The present invention relates to a method of and system for continuously processing liquid material such as liquid foodstuff or liquid medicine using a supercritical or subcritical fluid. The "processing" hereby includes: inactivation of enzymes and spores in and sterilization of liquid foodstuffs, liquid medicines or the like; and deodorization of liquid foodstuffs. The present invention also relates to a liquid material produced by the method or system according to the present invention.

BACKGROUND OF THE INVENTION

There are various kinds of foodstuffs containing enzymes there days, in which sake, beer and juice are typical examples. In general, a process of producing sake includes: first step where fermented rice is compressed and filtered to obtain shinshu (green sake); second step where this obtained green sake is sterilized by heating and then stored; third step where plural lots of stored sakes are properly mixed to determine the sake quality and the alcohol content is adjusted to the standards; and fourth step where the thus adjusted sake is again sterilized by heating and then bottled or packed. As described above, sake undergoes the heat-treatment twice in the second and fourth steps in the manufacturing process to inactivate and kill bacteria therein, whereby the sake quality is prevented from deteriorating during market circulation. A problem here is that the fresh aroma of green sake is sharply reduced by the heat-treatments. Therefore, a non-heat-treated sake, or fresh sake, preserving the fresh taste and aroma, is in great demand. To meet the demand, the fresh sake is also circulated in the market by keeping it at low temperature. Such a non-heat-treated sake, however, contains enzymes such as α-amylase and protease, which deteriorate the sake quality. The increased circulation cost due to the low temperature circulation is anther problem.

As for muddled fruit drinks such as orange juice, it is necessary to inactivate pectin esterase in order to maintain the muddled state of the drink. Since pectin esterase is stable to heat, a heat-treatment for inactivating this enzyme must be conducted at high-temperature (88–99° C., or 120° C.). The heat-treatment at such high temperature, however, deteriorates the relish of the drink.

Regarding the above-described problems, some of the inventors of the present application proposed a method of processing liquid foodstuff containing enzymes, as disclosed in Japanese Unexamined Patent Publication No. H07-170965, where the enzymes are inactivated by contacting carbon dioxide in a supercritical state. According to this method, the liquid foodstuff containing enzymes is contained in a processing chamber, which is then sealed, and supercritical fluid of carbon dioxide is supplied into the sealed processing chamber. The temperature and pressure inside the processing chamber are kept appropriately under preset conditions, and the supercritical fluid is supplied into the chamber through a filter whereby the fluid is formed into micro-particles having diameters of about a few hundreds of micrometers or less. Thus, the supercritical fluid of carbon dioxide effectively dissolves into the liquid foodstuffs. This method not only improves the inactivating efficiency, but also is highly safe since it is only carbon dioxide that contacts the liquid foodstuff. By this method, simultaneously, microorganisms such as bacteria, yeast fungus or mold can be killed.

Also, some of the inventors of the present application proposed a continuous processing system constructed so that the inactivating and sterilizing process is carried out more effectively and with less quality deterioration (Japanese Unexamined Patent Publication No H09-206044 or corresponding U.S. Pat. No. 5,704,276). With this continuous processing system, the liquid foodstuff is continuously supplied into a processing chamber from its bottom while maintaining the inside of the chamber at preset temperature and pressure. Carbon dioxide in a supercritical state is continuously supplied into the processing chamber through a mesh filter provided at the bottom of the chamber. In the upper part of the processing chamber is located a take-out port at a level a little lower than the level of the liquid foodstuff, from which the product (or processed liquid foodstuff) is taken out. In the processing chamber, the liquid foodstuff and micro-particles of the supercritical fluid flow upwards in parallel, contacting each other, whereby the enzymes are effectively inactivated. The processing chamber also has a drainage port for draining the supercritical fluid from the chamber. The supercritical fluid taken out from the drainage port is returned to a carbon dioxide source to be used again. Since this system can continuously process a liquid foodstuff, it is suitably used in a drink or food factory where a large amount of liquid foodstuff is to be processed.

With the above-described continuous processing system, the inactivation of enzymes in or sterilization of liquid materials is efficiently carried out. The practical use of this system, however, is difficult because of the cost problem as follows.

In the above continuous processing system, the temperature of the processing chamber must be kept at or above 31.1° C. in order to maintain the carbon dioxide in the supercritical state. Such a condition relating to temperature, however, is not preferable in view of efficient dissolution of carbon dioxide into the liquid foodstuff because carbon dioxide less dissolves into a liquid foodstuff as the temperature is higher. Hence, for obtaining an adequate inactivating and sterilizing effect, it is necessary to keep the liquid foodstuff and the supercritical fluid flowing in parallel for a considerably long time (from a few minute to a few tens of minutes, for example). Such a long processing time can only be realized by using a processing chamber of a large capacity. Also, a warming apparatus is necessary to the processing chamber to maintain the above-mentioned temperature. Another warming apparatus is necessary for moderately warming the liquid foodstuff in the course of transfer from a source to the processing chamber, because the reaction in the processing chamber is slow if the temperature of the liquid foodstuff supplied into the processing chamber is low. Thus, the continuous processing system becomes inevitably large and requires a large installation space, and the construction cost should be high.

Another problem lies with respect to the temperature of the processing chamber. Though, in the above-described system, the temperature in the processing chamber is considerably lower than the temperature for inactivating enzymes by heat, the temperature; is higher than a normal ambient temperature. It is possible therefore that the quality of the liquid foodstuff is deteriorated while the liquid foodstuff is kept at such a temperature for the process contains enzymes of high activity, and the enzymes badly affect the quality of the juice in the processing chamber before they are completely inactivated.

For solving the above-described problems, one object of the present invention is to propose a method of and system for continuously processing liquid materials with a small-sized processing chamber (or chambers) and a minimum number of warming apparatuses. The present invention also proposes a liquid material processed by such method or system.

SUMMARY OF THE INVENTION

In the above-described continuous processing system, the process of dissolving carbon dioxide into the liquid material and the process of changing the carbon dioxide into a supercritical state and maintaining the state are carried out simultaneously in the processing chamber. In contrast to that in the method or system according to the present invention the two processes are carried out separately in time and space.

Thus, in a method of continuously processing a liquid material such as liquid foodstuff with a supercritical or subcritical fluid, the process according to the present invention includes:

a) a dissolving stage where a liquefied carbon dioxide is continuously supplied into the liquid material while the liquid material is continuously supplied to dissolve the liquefied carbon dioxide into the liquid material;

b) a critical processing stage where the liquid material with the liquefied carbon dioxide dissolved therein is kept under a preset temperature-and-pressure condition so that the carbon dioxide is brought into a supercritical or subcritical state; and c) a pressure-reducing stage where the pressure of the liquid material after passing the critical processing step is reduced rapidly to remove the carbon dioxide and the liquid material is retrieved as a product.

Also, in a system of continuously processing a liquid material with a supercritical or subcritical fluid, the system according to the present invention includes:

a) a material supply line for continuously supplying the liquid material;

b) a carbon dioxide supply line for continuously supplying a liquefied carbon dioxide;

c) a dissolving part where the liquefied carbon dioxide supplied through the carbon dioxide supply line is dissolved into the liquid material while the liquid material is continuously supplied through the material supply line;

d) a critical processing part where the liquid material taken out from the dissolving part with the liquefied carbon dioxide dissolved therein is kept under a preset temperature-and-pressure condition so that the carbon dioxide is brought into a supercritical or subcritical state; and e) a pressure reducing part where the pressure of the liquid material after passing the critical processing part is reduced rapidly to remove the carbon dioxide and the liquid material is retrieved as a product.

The liquid material according to the present invention is characterized in that it is processed and retrieved by the method or system according to the present invention.

By the method or system according to the present invention, a liquid material such as a liquid foodstuff or liquid medicine is continuously supplied through the material supply line into the dissolving part, while a cooled and liquefied carbon dioxide is continuously supplied through the carbon dioxide supply line into the dissolving part. A mesh filter having a small mesh size may be placed at the exit of the carbon dioxide in the dissolving part. In this case, when the liquefied carbon dioxide passes through the filter, the carbon dioxide is formed into micro-particles and dissolves into the liquid material. High-speed mixers, ultrasonic generators or other devices may be used for improving the contacting efficiency of the carbon dioxide and the liquid material. It is desirable to cool the dissolving part because, as generally known, the solubility of liquefied carbon dioxide in a liquid is higher as the ambient temperature is lower. Even at a room temperature, an adequate amount of liquefied carbon dioxide dissolves into the liquid material in a short time period. The dissolving efficiency is high in winter since the ambient temperature is low.

For example, the dissolving part is constructed using a dissolving chamber, where an entrance for the liquid material from the material supply line and another entrance for the liquefied carbon dioxide from the carbon dioxide supply line are located at the bottom of the dissolving chamber, and an exit for the liquid material is located at about the level of the liquid material of the upper part of the dissolving chamber. Owing to this construction, the liquid material introduced from the bottom of the dissolving chamber flows upwards in the dissolving chamber, and the micro-particles of the liquefied carbon dioxide flow in the same direction. Thus given a large contact area, the liquefied carbon dioxide efficiently dissolves into the liquid material.

The dissolving part may be constructed using a pipe provided as the material supply line (a material supply pipe), where the liquefied carbon dioxide is made to dissolve into the liquid material by discharging the liquefied carbon dioxide into the liquid material. Such a construction is advantageous in that the system can be made smaller in size because there is no need to provide a dissolving chamber or the like.

One method of improving the efficiency of dissolving the carbon dioxide into the liquid material is that a mesh filter is placed in the material supply pipe and the liquefied carbon dioxide is made to pass through the mesh filter so that the liquefied carbon dioxide is formed into micro-particles in the liquid material. Another method is that a mixer is placed in the material supply pipe and the liquefied carbon dioxide is discharged into the liquid material at upstream of the mixer. As described above, the solubility of liquefied carbon dioxide in a liquid is higher as the ambient temperature is lower. Accordingly, it is preferable to cool the material supply pipe at the part where the filter or mixer is placed. In this case, however, it is not necessary to cool the material supply pipe to an abnormally low temperature because an adequate amount of liquefied carbon dioxide dissolves into the liquid material in a short time period even at the room temperature. Naturally, therefore, the dissolving efficiency is high in winter since the ambient temperature is low. Therefore, a considerable advantage is obtained by simply keeping the temperature of the above-mentioned part of the material supply pipe.

The liquid material in which the liquefied carbon dioxide is dissolved is then transferred from the dissolving part to the critical processing part. In the critical processing part, the liquid material with the liquefied carbon dioxide dissolved therein is kept under a preset temperature-and-pressure condition so that the carbon dioxide is brought into a supercritical or subcritical state. A preferable temperature condition is 30–80° C., more preferably 30–50° C., and a preferable pressure condition is 40–400 atm, more preferably 100–300 atm. Under such a condition, the liquefied carbon dioxide dissolved in the liquid material is rapidly brought into a supercritical or subcritical state. The time period for keeping the liquid material under such a condition may be as long as 1 minute or so. Therefore, even though the temperature in the critical processing part is higher than the room temperature, deterioration of the quality of liquid material due to the heat is minimized.

After being processed in the critical processing part, the liquid material is transferred to the pressure-reducing part, where the pressure of the liquid material is rapidly reduced (pressure-reducing process). Then, carbon dioxide having permeated into the enzymes swells rapidly, whereby the protein of the enzymes is destroyed and the enzymes are inactivated. Similarly, various kinds of microorganisms are also killed. The carbon dioxide in the liquid material thus turns to gas and is discharged from the liquid material. After that, the liquid material is retrieved as a product. In the above-described pressure-reducing process, it is important to regulate the pressure-reducing speed. When, for example, a pressure control valve having an orifice is used for the pressure reduction, the pressure-reducing speed should be determined so that every molecule of the liquid material passes through the orifice within 20 milliseconds, more preferably within 10 milliseconds.

Typical liquid materials which can be processed by the method or system according to the present invention are: fermented or brewed liquid foodstuffs such as green sake, beer, wine, soy sauce; juices; cooling beverages, etc. Some juices are produced from fruits such as apple, grape or orange, and other juices are produced from vegetables such as tomatoes, and the process of the present invention is generally applicable to all kinds of juices. Not only liquid foodstuffs as listed above, but also liquid medicine such as transfusion liquids, blood derivatives nutritious drinks can be processed by the method or system according to the present invention.

As described above, by the method or system according to the present invention, the process of dissolving the liquefied carbon dioxide into the liquid material and the process of bringing the carbon dioxide into a supercritical or subcritical state are separately carried out. Owing to this construction, each process is carried out with a very high efficiency, and the total processing time is greatly shortened compared to the processing time required by the conventional continuous processing method or system. Since neither the large-sized processing chamber nor the warming apparatus is necessary, the system can be designed smaller in size. In the critical processing step, the temperature can be optimized, so that a higher efficiency is obtained with respect to the inactivation of enzymes in and the sterilization of the liquid material. The time period of keeping the liquid material at high temperature is short, so that there is little or no possibility of damaging fresh aroma of the product.

BRIEF DESCRIPTION OF THE DRAWINGS

FIG. 2 shows a table showing the result of a test where the proportion of active enzymes remaining in a liquid material processed by the system of FIG. 1 were investigated.

DETAILED DESCRIPTION OF PREFERRED EMBODIMENTS

Continuous processing systems embodying the present inventions are described referring to the attached drawings.

Figure 1:
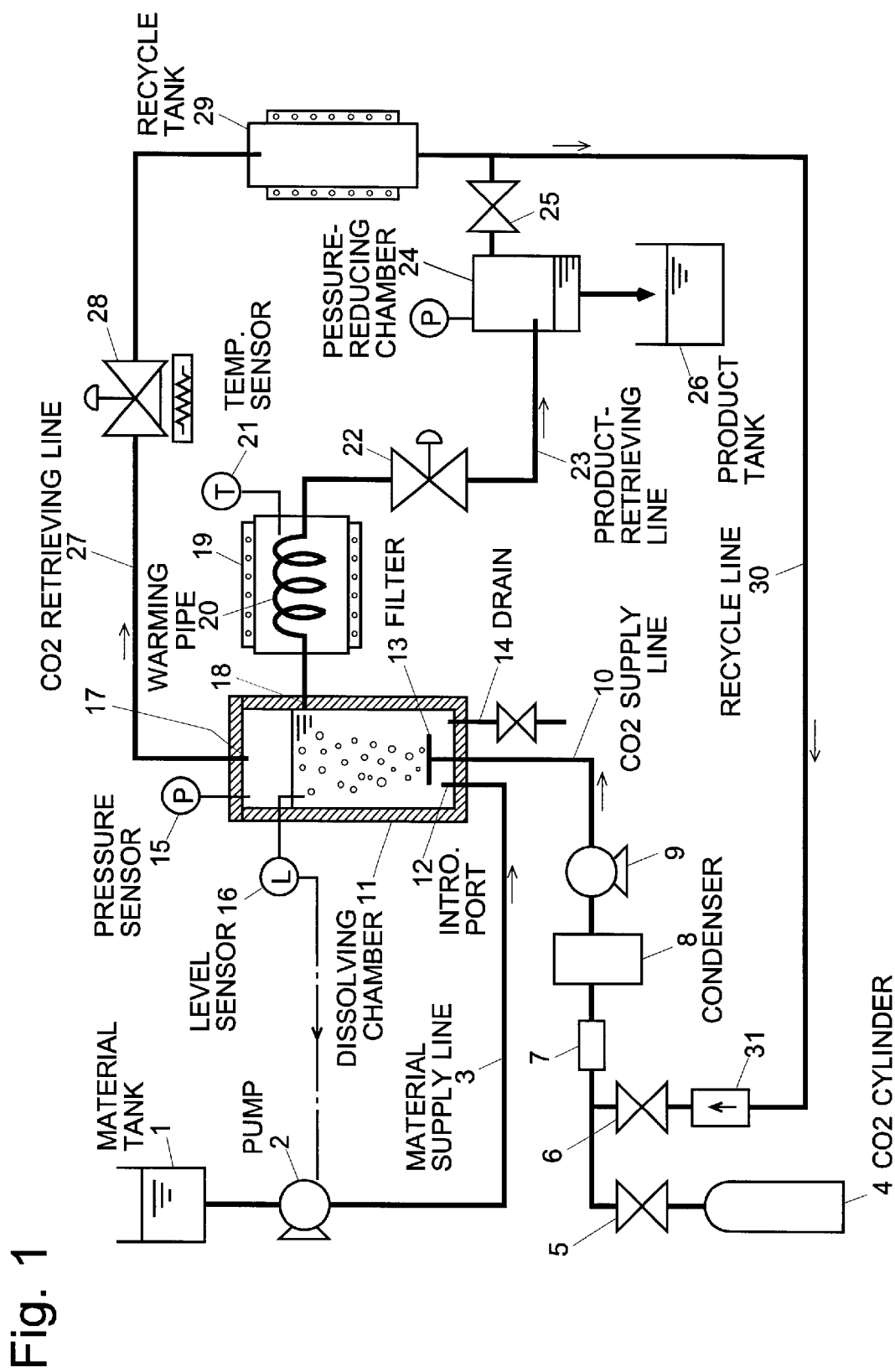
FIG. 1 shows a construction of a continuous enzyme-inactivating system embodying the present invention.

FIG. 1 shows a continuous enzyme-inactivating system embodying the present invention. In this system, a liquid material is stored in a material tank 1, and a material supply line 3 connects the bottom of the material tank 1 and a dissolving chamber 11. A pump 2 for pressurizing and transferring the liquid material is disposed in the line 3. By appropriately determining the driving condition of the pump 2, the liquid material can be continuously supplied to the dissolving chamber 11 at a desired flow rate.

A carbon dioxide supply line ($CO_2$ supply line) 10 connects a liquefied carbon dioxide cylinder ($CO_2$ cylinder) 4 and the bottom of the dissolving chamber 11. A valve 5, a line filter 7, a condenser 8 and a pump 9 are disposed in the $CO_2$ supply line 10. If the liquefied carbon dioxide turns to gas in the course of the line, the condenser 8 cools and liquefies the carbon dioxide gas. The condenser 8 also liquefies carbon dioxide gas supplied from a recycle line 30 (which will be described later). Thus, liquefied carbon dioxide is pressurized by the pump 9 and is supplied to the dissolving chamber 11.

The dissolving chamber 11 is a pressure-resistant container. An introduction port 12 is located at the bottom of the dissolving chamber 11, to which the exit of the material supply line 3 is connected, and A mesh filter 13 having micro holes is placed at the exit of the $CO_2$ supply line 10. For the purpose of efficiently dissolving the liquefied carbon dioxide into the liquid material, it is preferable to discharge the liquefied carbon dioxide in the form of micro-particles as minute as possible. Thus, the mesh size of the filter 13 should be preferably smaller than 100 $\mu$m, more preferably smaller than 20 $\mu$m. A drain 14 having a valve is connected to the bottom of the dissolving chamber 11 for draining liquid from the chamber. In the upper part of the dissolving chamber 11, a take-out port 18 is located at about a level of the liquid material. The liquid material introduced from the introduction port 12 flows upwards in the dissolving chamber 11 and is taken out from the take-out port 18 to the outside when it comes to the surface level of the liquid material.

The dissolving chamber 11 is equipped with a level sensor 16. The output signal of the level sensor 16 is used for a feedback control of the pump 2, so that the level of the liquid material is kept at a constant level in the dissolving chamber 11. Instead of using the level sensor 16, the level of the liquid material may be kept at a constant level by, for example, controlling the flow rates of supplying the liquid material from the introduction port 12 and of taking out the liquid material from the take-out port 18 to be equal to each other. When the level of the liquid material is kept at a constant level, the time period for the liquid material to pass through the dissolving chamber 11 is also kept at a constant value, so that the carbon dioxide evenly and stably dissolves into the liquid material, as will be described later.

The top of the dissolving chamber 11 is closed by a cover having a $CO_2$ drainage port 17. As will be described later, liquefied carbon dioxide is made to dissolve into the liquid material in the dissolving chamber 11, where a portion of the liquefied carbon dioxide may change to a supercritical or subcritical fluid, depending on the condition. The density of the supercritical or subcritical fluid is smaller than that of the liquid material, so that the supercritical or subcritical fluid can be taken out from the $CO_2$ drainage port 17 located higher than the level of the liquid material.

A spiral warming pipe 20 is connected to the take-out port 18. The warming pipe 20 is held in an constant-temperature oven having a warming apparatus (or heater) 19, or in a metal block for maintaining temperature. The temperature of the warming pipe 20 is monitored with a temperature sensor 21. The temperature monitored with the temperature sensor 21 is used for a feedback control of the heater 19 so that the temperature of warming pipe 20 is kept at about a constant temperature.

The pressure in the dissolving chamber 11 is monitored with a pressure sensor 15. Since the dissolving chamber 11 and the warming pipe 20 are placed between the pumps 2, 9 and pressure control valves 22, 28, the pressure can be regulated at a preset value by controlling the power of the pumps 2, 9 for supplying the liquid material and the liquefied carbon dioxide and the opening of the pressure control valves 22, 28.

A product-retrieving line 23 having a pressure control valve 22 for reducing pressure connects the exit of the warming pipe 20 and a pressure-reducing chamber 24. In the pressure-reducing chamber 24, the carbon dioxide dissolved in the product (the processed liquid material) turns to gas, and the carbon dioxide gas taken out from the chamber 24 is returned through a valve 25 to the recycle line 30. The product stored in the pressure-reducing chamber 24 is transferred to a product tank 26. In the process of gasifying the carbon dioxide, the carbon dioxide deprives the liquid material of heat, so that the liquid material, which is once warmed in the warming pipe 20, is cooled in the pressure-reducing chamber 24. Thus, a product whose temperature is equal to or lower than the room temperature is obtained.

A $CO_2$ retrieving line 27 connects the carbon dioxide drainage port 17 and a recycle tank 29 via the pressure control valve 28. The supercritical or subcritical fluid of carbon dioxide sent to the $CO_2$ retrieving line 27 undergoes a pressure reduction at the pressure control valve 28, changes to a carbon dioxide gas and is retrieved into the recycle tank 29. The recycle tank 29 is connected to the $CO_2$ supply line 10 by the recycle line 30 having a check valve 31 and a valve 6. The recycle tank 29 is available as an alternative carbon dioxide source in place of the $CO_2$ cylinder 4. By this construction, recycled carbon dioxide is primarily used for the process, and the carbon dioxide contained in the $CO_2$ cylinder 4 is used merely for making up for a shortage of carbon dioxide. Thus, the liquefied carbon dioxide stored in the $CO_2$ cylinder 4 is saved.

With the above-described system, the process of inactivating enzymes is conducted as follows. The liquid material is continuously supplied from the introduction port 12 into the dissolving chamber 11. The liquefied carbon dioxide introduced from the $CO_2$ supply line 10 passes through the filter 13, where the liquefied carbon dioxide is formed into micro-particles corresponding to the mesh size of the filter 13 and is discharged into the liquid material. Thus, the micro-particles of the liquefied carbon dioxide produced by the filter 13 contact the liquid material immediately after the introduction of the liquid material, so that the liquefied carbon dioxide efficiently dissolves into the liquid material.

It is preferable to cool the dissolving chamber 11 because the liquefied carbon dioxide dissolves more efficiently as the temperature is lower. An adequately high solubility is obtained even by simply keeping the dissolving chamber 11 at the room temperature.

The liquid material with the liquefied carbon dioxide dissolved therein flows upwards in the dissolving chamber 11 and reaches the take-out port 18. For obtaining an adequate effect in inactivation of enzymes and sterilization, it is desirable to dissolve the carbon dioxide into the liquid material as much as possible. When the object of the process is to kill a hard-to-kill bacteria, it is essential to keep an adequate time period for the liquefied carbon dioxide to act on the bacteria in the liquid material. One method of keeping the action time of the liquefied carbon dioxide longer is to dispose baffle plates in the dissolving chamber 11. Another method is to dispose another chamber (retaining chamber) for retaining the liquid material with the liquefied carbon dioxide dissolved therein for a certain time period between the dissolving chamber 11 and the warming pipe 20. In the case of using the retaining chamber, it is possible to discharge the liquefied carbon dioxide into the liquid material also in the retaining chamber, which, however, is merely optional. When the liquefied carbon dioxide is discharged into the liquid material also in the retaining chamber, it is possible to make the liquid material and the liquefied carbon dioxide contact with each other in a counter-flow manner. By such a method, the liquid material is properly agitated or stirred by the liquefied carbon dioxide (or by micro-particles thereof), so that the liquid material evenly dissolves into the liquid material.

The liquid material taken out from the take-out port 18 is introduced into the warming pipe 20. There, liquefied carbon dioxide not dissolved into but simply mixed with the liquid material is also introduced into the warming pipe 20 with the liquid material, which is no problem. Using the heater 19, the temperature of the warming pipe 20 is kept at about 30–40° C. The pressure in the warming pipe 20 (and also in the dissolving chamber 11) is kept at 100–300 atm. Under such a temperature-and-pressure condition, the liquefied carbon dioxide rapidly changes to a supercritical fluid. The liquid material passes through the spiral warming pipe 20 in about 1 minute. When the liquefied carbon dioxide dissolved into the liquid material changes to the supercritical fluid, a part of the enzymes contained in the liquid material are destroyed, and a part of microorganisms are killed. The effect obtained here, however, merely covers a part of the whole.

After that, when the liquid material passes through the pressure control valve 22 and reaches the pressure-reducing chamber 24, the carbon dioxide is released from the supercritical state due to a rapid pressure reduction, turns to gas and rapidly swells. At this moment, the proteins of the enzymes are destroyed, and the microorganisms are killed. Thus, the enzymes and spores in the liquid material are inactivated, and the liquid material is sterilized. The processed product is collected in the product tank 26. The product collected in the product tank 26 contains only a small percentage of active enzymes and no undesirable microorganisms. The temperature of the product collected is low, as explained above. Since the liquid material is not heated in the process of gasifying the carbon dioxide in the pressure-reducing chamber 24, aroma component contained in the liquid material hardly vaporizes, and its relish is hardly damaged.

The result of a test for verifying the inactivation effect by the continuous enzyme-inactivating system of FIG. 1 is described. FIG. 2 shows a table of the result of the test where the liquid material after the process was examined regarding the percentage of active enzymes remaining therein. The result obtained with the system of FIG. 1 is shown as "Present Case". For the purpose of comparison, the result obtained with a conventional continuous processing system using a supercritical or subcritical fluid (as disclosed in Japanese Unexamined Patent Publication No. H09-206044) is shown as "Reference Case 1", and the result obtained with the conventional heat-treatment method is shown as "Reference Case 2".

The amount of liquid material supplied is 20 kg/h, and the amount of carbon dioxide supplied is 1.6 kg/h. As for temperature, pressure and processing time, the present case is conducted so that the critical processing step is carried out for 1 minute under the temperature of 50° C. and pressure of 250 atm. In the Reference Case 1, the critical processing step is carried out for 15 minutes under the temperature of 40° C. and pressure of 250 atm. In the Reference Case 2, the heat-treatment is carried out for 1 minute under the temperature of 85° C.

As understood from FIG. 2, the inactivation effect obtained by either of the Present Case and Reference Case 1 using the supercritical or subcritical fluid is higher than the effect obtained by the heat-treatment. No significant difference in the inactivation effect is detectable between the former two cases. This means that the method according to the present case where the processing time is as short as 1 minute yields an effect comparable to the effect obtained by the method of the reference case 1 where the processing time is as long as 15 minutes.

In addition to the above test, the number of spores remaining in the microorganisms was measured after the process. By this test, it was confirmed that no spore was found in eight kinds of Bacillus genus including Bacillus subtilis. This proves that microorganisms can be killed completely by the method of the present case.

When the system is constructed for the purpose of processing a liquid material that is desired to hold aroma component as much as possible (such as fruit juices), another line may be provided through which at least a part of the supercritical fluid of the carbon dioxide taken out from the carbon dioxide drainage port 17 is introduced to the pressure-reducing chamber 24. The supercritical fluid of carbon dioxide introduced through the line into the pressure-reducing chamber 24 turns to gas, where aroma component captured in the carbon dioxide in the dissolving chamber 11 is released. The released aroma component again dissolves into the product retrieved in the pressure-reducing chamber 24. Thus, the retrieved product resultantly contains more aroma component.

Figure 3:
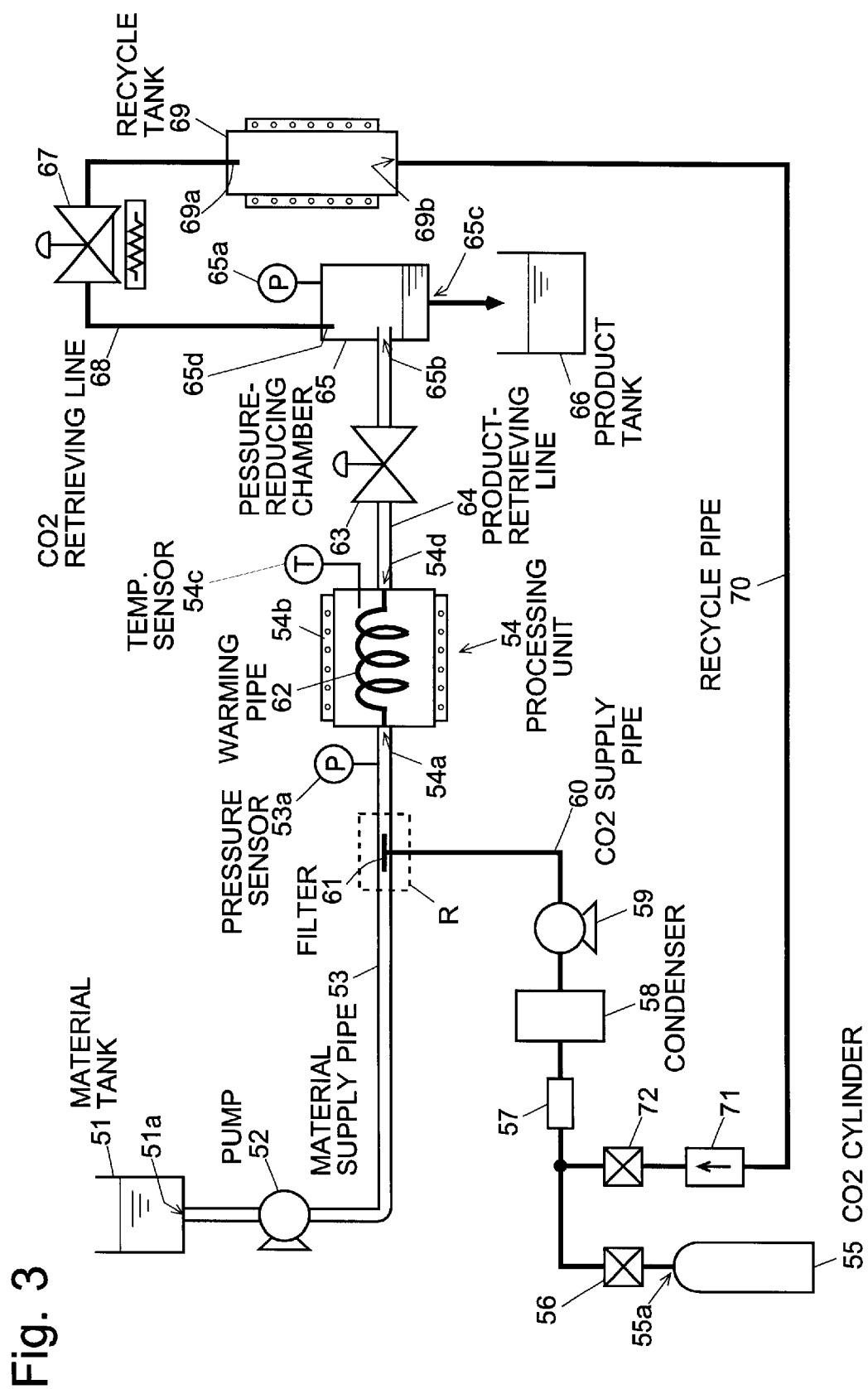
FIG. 3 shows a construction of another continuous enzyme-inactivating system embodying the present invention.
Figure 4:
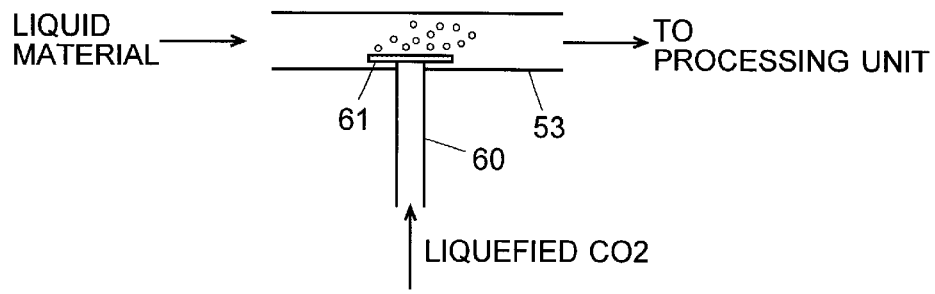
FIG. 4 is an enlarged view of a part (enclosed by a rectangle R in FIG. 3) of a material supply pipe where a filter is provided.

FIG. 3 shows the construction of another continuous enzyme-inactivating system, and FIG. 4 is an enlarged view of a part of the system enclosed in rectangle R in FIG. 3.

In the system of FIG. 3, a liquid material to be processed is stored in a material tank 51 having an outlet 51a. A material supply pipe 53 in which a pump 52 is disposed connects the outlet 51a of the material tank and an inlet 54a of a processing unit 54. Liquefied carbon dioxide to be used in a process is stored in a carbon dioxide cylinder ($CO_2$ cylinder) 55. To the outlet 55a of the $CO_2$ cylinder 55 is connected an end (entrance end) of a carbon dioxide supply a pipe ($CO_2$ supply pipe) 60, in which a valve 56, a line filter 57, a condenser 58 and a pump 59 are disposed. The other end (exit end) of the $CO_2$ supply pipe 60 is inserted into the material supply line 53 through the side wall of the material supply line 53. A mesh filter 61 having micro holes is placed near the exit end of the $CO_2$ supply pipe 60. The material supply pipe 53 is equipped with a pressure sensor 53a for detecting the pressure inside at a point close to the inlet 54a of the processing unit 54.

The processing unit 54 is a constant-temperature oven having a heater 54b and a temperature sensor 54b. A spiral warming pipe 62 is held in processing unit 54. In the processing unit 54, an end of the warming pipe 62 leads to the inlet 54a and the other end leads to the outlet 54d of the processing unit 54. To the outlet 54d of the processing unit 54 is connected an end of a product-retrieving line 64 having a pressure control valve 63. The other end of the product-retrieving line 64 is connected to an inlet 65b provided in the side wall of a pressure-reducing chamber 65 having a pressure sensor 65a. The pressure-reducing chamber 65 has a product take-out port 65c at its bottom, and a product tank 66 is placed right under the port 65c. A $CO_2$ drainage port 65d is located in the upper part of the pressure-reducing chamber 65, and an end of a $CO_2$ retrieving line 68 in which a pressure control valve 67 is disposed is connected to the drainage port 65d. The other end of the $CO_2$ retrieving line 68 is connected to a gas inlet 69a of a recycle tank 69. The recycle tank 69 has a gas outlet 69b at its bottom, and an end of a recycle pipe 70 is connected to the outlet 69b. A check valve 71 and a valve 72 are disposed in the recycle pipe 70. The other end of the recycle pipe 70 is connected to the $CO_2$ supply pipe 60 between the valve 56 and the line filter 57.

Though not shown in the Figure, the system includes a controller for controlling each part of the system based on the outputs of the pressure sensor and/or temperature sensor. For example, the controller performs as a temperature controller for maintaining the temperature in the processing unit 54 at a preset temperature by a feedback control of the heater 54b based on the output of the temperature sensor 54c. Also, the controller performs as a pressure controller for maintaining the pressure in the warming pipe 62 and the pressure in the pressure-reducing chamber 65 by a feedback control of the pumps 52, 59 and the pressure control valves 63, 67 based on the outputs of the pressure sensors 53a, 65a. Regarding the pressure control, it should be noted that the controller controls the above-mentioned parts so that the pressure in the material supply pipe 53 detected with the pressure sensor 53a (this pressure is equal to the pressure in the warming pipe 62) is kept at about 100–300 atm, and that the pressure in the pressure-reducing chamber 65 detected with the pressure sensor 65a is kept at a pressure far lower than that (about 240 atm, for example).

The above-described system operates as follows. First, at the start of the operation, the valve 56 disposed in the $CO_2$ supply pipe 60 is opened, and the two pumps 52 and 59 are energized. By the operation of the pump 52, the liquid material stored in the material tank 51 is continuously supplied to the liquid material supply pipe 53. By the operation of the pump 59, the liquefied carbon dioxide stored in the $CO_2$ cylinder 55 is supplied through the $CO_2$ supply pipe 60. Even when the liquefied carbon dioxide having exited the $CO_2$ cylinder 55 turns to gas in the $CO_2$ supply pipe 60, the carbon dioxide gas is condensed by the condenser 58 and turns to liquid. Thus, the liquefied carbon dioxide is stably supplied to the material supply pipe 53.

The liquefied carbon dioxide flowing through the $CO_2$ supply pipe 60 passes through the filter 61 at the exit end of the pipe 60, where it is formed into micro-particles and discharged into the liquid material (FIG. 4). The micro-particles of the liquefied carbon dioxide produced by the filter 61 contact the liquid material immediately after the introduction of the liquid material, so that the liquefied carbon dioxide efficiently dissolves into the liquid material. For the purpose of efficiently dissolving the liquefied carbon dioxide into the liquid material, it is preferable to supply the liquefied carbon dioxide in the form of particles as minute as possible. Thus, the mesh size of the filter 13 preferably should be smaller than 100 $\mu$m, more preferably smaller than 20 $\mu$m. Also, it is preferable to cool the material supply pipe 53 at least at the part where the filter 61 is disposed inside because, in general, the solubility of a gas into a liquid is higher as the temperature is lower. It is not necessary to cool the above-mentioned part to an abnormally low temperature. An adequately high solubility is obtained even by simply keeping the above-mentioned part at the room temperature.

Figure 5A:
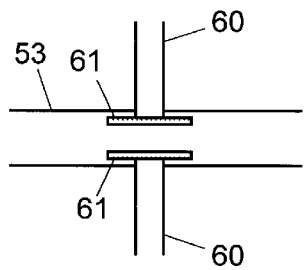
FIGS. 5A and 5B show plural filters provided in the material supply pipe.
Figure 5B:
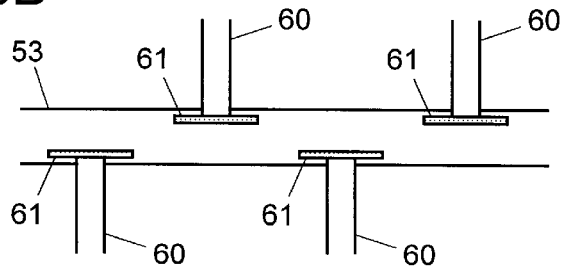

In the example of FIG. 4, one filter 61 is used in the material supply pipe 53. It is possible to use plural filters 61 in the material supply pipe 53. FIG. 5A shows an example of such a construction, where two filters 61 are placed to face to each other in the material supply pipe 53. FIG. 5B shows another example, where four filters 62 are alternately placed in the material supply pipe 53 along the flow direction of the liquid material. By using plural filters as described above, the dissolving efficiency of the liquefied carbon dioxide is improved. The pipes for transferring the carbon dioxide to each of the filters 61 may be constructed by branching the $CO_2$ supply pipe 60 at downstream of the pump 59.

The liquid material with the liquefied carbon dioxide dissolved therein is introduced through the inlet 54a of the processing unit 54 into the warming pipe 62. There, liquefied carbon dioxide not dissolved into but simply mixed with the liquid material is also introduced into the warming pipe 62 with the liquid material, which is no problem. Using the heater 54b, the temperature of the warming pipe 62 is kept at about 30–40° C. The pressure in the warming pipe 62 is kept at 100–300 atm. Under such a temperature-and-pressure condition, the liquefied carbon dioxide rapidly changes to a supercritical fluid. The liquid material passes through the spiral warming pipe 62 in about 1 to a few minutes. When the liquefied carbon dioxide dissolved into the liquid material changes to the supercritical fluid, a part of the enzymes contained in the liquid material are destroyed, and a part of microorganisms are killed. The effect obtained here, however, merely covers a part of the whole.

After that, the liquid material passes through the pressure control valve 64 and reaches the pressure-reducing chamber 65. There, the liquid material is released from the supercritical state due to a rapid pressure reduction, turns to gas and rapidly swells. At this moment, the proteins of the enzymes are destroyed, and the microorganisms are killed. Thus, the enzymes and spores in the liquid material are inactivated, and the liquid material is sterilized. As a result of the pressure reduction, the temperature of the liquid material rapidly decreases to a temperature equal to or lower than the room temperature. The processed product is taken out from the product take-out port 65c and is collected in the product tank 66. The product thus collected in the product tank 66 contains only a small percentage of active enzymes and no undesirable microorganisms. Since the liquid material is not heated in the process of gasifying the carbon dioxide in the pressure-reducing chamber 65, aroma component contained in the liquid material hardly vaporizes, and its relish is hardly damaged.

As described above, most of the carbon dioxide dissolved in the liquid material turns to gas and is separated from the liquid material, so that the product taken out from the product take-out port 65c contains little carbon dioxide. Depending on the type of product, however, it is necessary to remove the carbon dioxide as completely as possible. In the case where such a product is to be produced, it is preferable to employ a deaerating unit for deaerating the product taken out from the product take-out port 65c of the pressure-reducing chamber 65. The deaerating unit may be constructed based on conventional deaerating methods, such as pressure reduction (where a gas dissolved in a liquid is extracted by containing the liquid in an airtight chamber and evacuating the chamber) or centrifugal separation.

The carbon dioxide gasified in the pressure-reducing chamber 65 flows through the $CO_2$ drainage port 65d into the $CO_2$ retrieving line 68, then passes through the pressure control valve 67 and reaches the recycle tank 69. After retrieving an adequate amount of carbon dioxide in the recycle tank 69, when the valve 72 disposed in the recycle pipe 70 is opened, the carbon dioxide stored in the recycle pipe 70 starts flowing through the recycle pipe 70 and the $CO_2$ supply pipe 60 due to the action of the pump 52, and is sent into the material supply pipe 53 again. Even when the carbon dioxide is present in a gas state in the recycle pipe 70, the carbon dioxide is liquefied by the condenser 58 and is sent to the material supply pipe 53. Thus, the recycle tank 69 may be used as a second carbon dioxide supply source. Therefore, after collecting an adequate amount of carbon dioxide in the recycle tank 69, it is preferable to mainly use the carbon dioxide stored in the recycle tank 69 and to use the carbon dioxide in the $CO_2$ cylinder 55 only for making up for a shortage of carbon dioxide. By such a method, the consumption amount of carbon dioxide is preferably suppressed.

Figure 6:
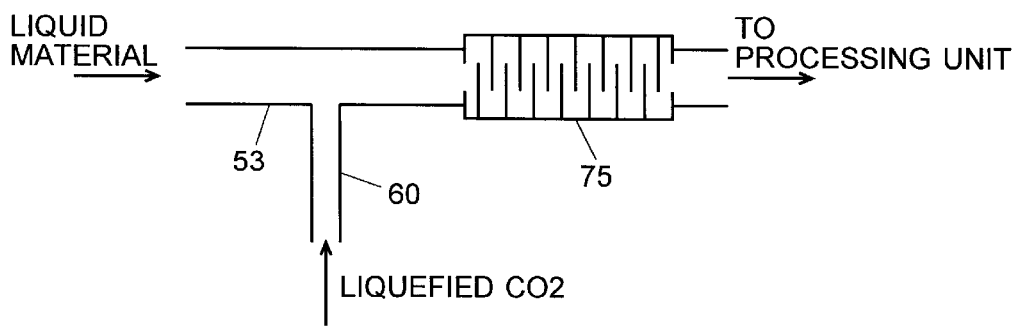
FIG. 6 shows an example of a dissolution-promoting mechanism constructed using a static mixer.

In the system of FIG. 3, the dissolution of the liquefied carbon dioxide into the liquid material is promoted by forming the liquefied carbon dioxide into micro-particles using a filter 61 disposed in the material supply pipe 53. It is of course possible to use other methods for promoting the dissolution of the liquefied carbon dioxide. FIG. 6 shows an example of a dissolution-promoting mechanism constructed using a static mixer. This mechanism is constructed by disposing a static mixer 75 in the material supply pipe 53 at downstream of a point where the $CO_2$ supply pipe 60 is connected to the material supply pipe 53. In the case where the static mixer is used, it is preferable to separate the $CO_2$ supply pipe 60 into branches at downstream of the pump 59 and connect the branches to the material supply pipe 53 so that the liquefied carbon dioxide is discharged into the liquid material at plural points, whereby the dissolving efficiency of the liquefied carbon dioxide is improved.

Figure 7:
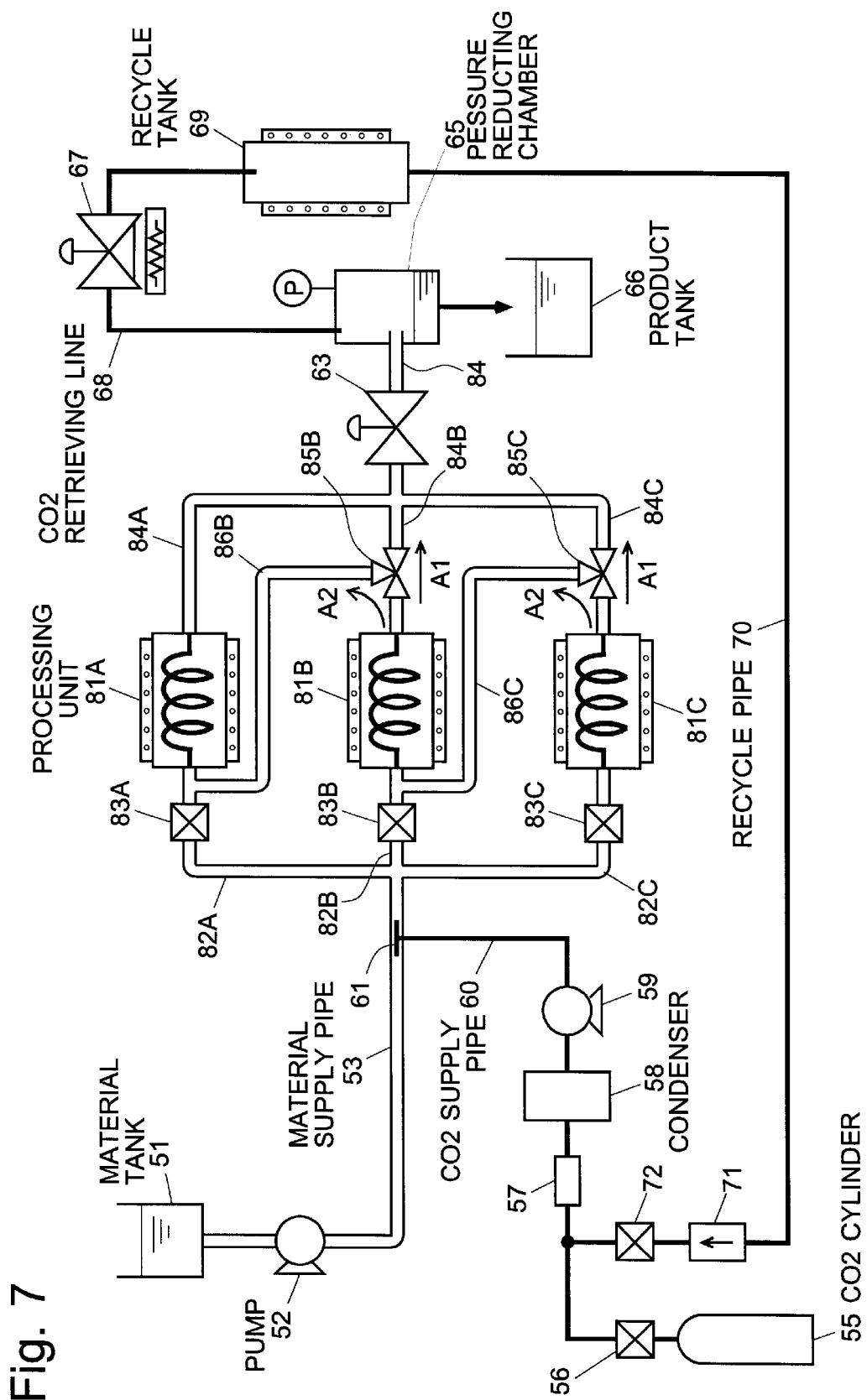
FIG. 7 shows an example of a continuous sterilizing system having plural processing units.

FIG. 7 shows an example of a continuous sterilization system having plural processing units. The system of FIG. 7 has three processing units 81A–81C, each of which is constructed similar to the processing unit 54 used in the system of FIG. 3. The material supply pipe 53 is separated into three branches 82A–82C at downstream of the filter 61. The ends of the three branches 82A–82C are connected to the inlets of the three processing units 81A–81C, respectively. Three valves 83A–83C are disposed in the three branches 81A–81C, respectively. Three product-retrieving branches 84A–84C are connected to the outlets of the three processing units 81A–81C, respectively. The three product-retrieving branches 84A–84C merges with each other into a product-retrieving line 84 at downstream. Three-way valves 85B and 85C are disposed in the two branches 84B and 84C, respectively. One port of the first three-way valve 85B is connected to the branch 82A by a bypass pipe 86B, and one port of the second three-way valve 85C is connected to the branch 82B by a bypass pipe 86C. Each of the three-way valves 85B and 85C is constructed so that its line direction is selectable between two directions denoted by arrows A1 and A2. A controller (not shown) controls the operations of the valves 83A–83C, the three-way valves 85B–85C, and the processing units 81A–81C (the heating operation of the heater of each of the processing unit, for example). The controller is equipped with an input device for allowing a user to input information relating to the process. For example, the information includes: kind and amount of the liquid material to be processed; type of the process (sterilization, inactivation, deodorization, etc.); kind of bacteria to be killed, if the type of the process selected is sterilization.

The system of FIG. 7 is constructed so that the number of the processing units and the configuration of the lines can be changed based on the information relating to the process that the user sends to the controller through the input device. For example, when the amount of liquid material to be processed is large, all the three valves 83A–83C are opened and the three-way valves 85B and 85C are set to the direction Al. By such a line configuration, the three processing units 81A–81C are connected in parallel, so that a large amount of liquid material can be processed simultaneously. When, for example, the target of the sterilization is hard-to-kill bacteria, the first and second valves 83A and 83B are closed, the third valve 83C is opened, and the three-way valves 85B and 85C are set to the direction A2. By such a configuration, the three processing units 81A–81C are connected in series and the processing time becomes accordingly long, so that even the hard-to-kill bacteria can be assuredly killed.

In the description of the system of FIG. 3, it is explained that the time period (or processing time) required for the liquid material to pass through the processing unit 54 is from 1 to a few minutes. When plural processing units are used as in the system of FIG. 7, the processing time in each of the processing unit may be shortened as long as the total processing time of the processing units is adequately long. Taking this into account, when the system includes plural processing units, each of the processing unit may be constructed using a small-sized processing chamber in place of the spiral warming pipe.

In the case where the critical processing part of the present invention is constructed using plural processing units as described above, the temperature of each of the processing units can be controlled independently. Accordingly, for example, the temperatures of the processing units may be determined so that the liquid material undergoes a sudden and great temperature change when it is transferred from one processing unit to the next, whereby bacteria that is weak against a temperature change is shocked and inactivated. It is also possible to determine the pressure to change from one processing unit to the next.

The dissolving part may be also constructed using plural units (dissolving units), each of which is independently operative.

Figure 8:
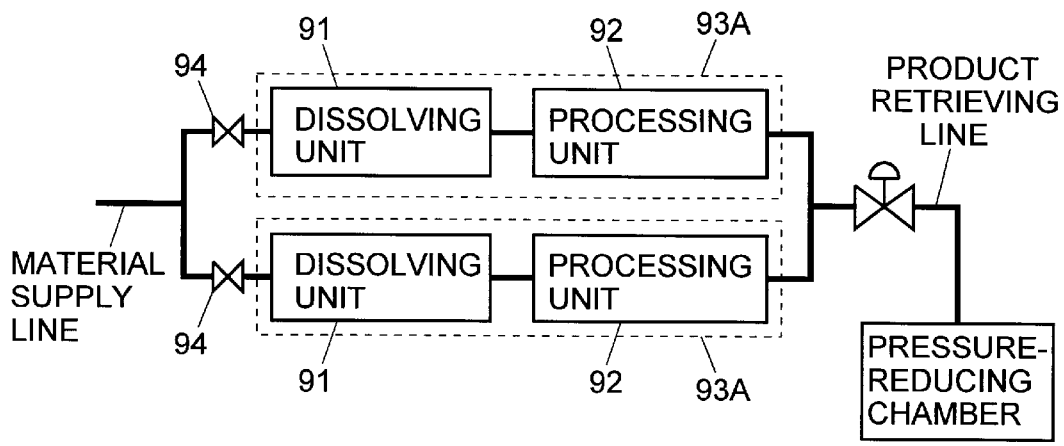
FIGS. 8 and 9 show other examples of the system according to the present invention where a part of the system is constructed using plural units.
Figure 9:
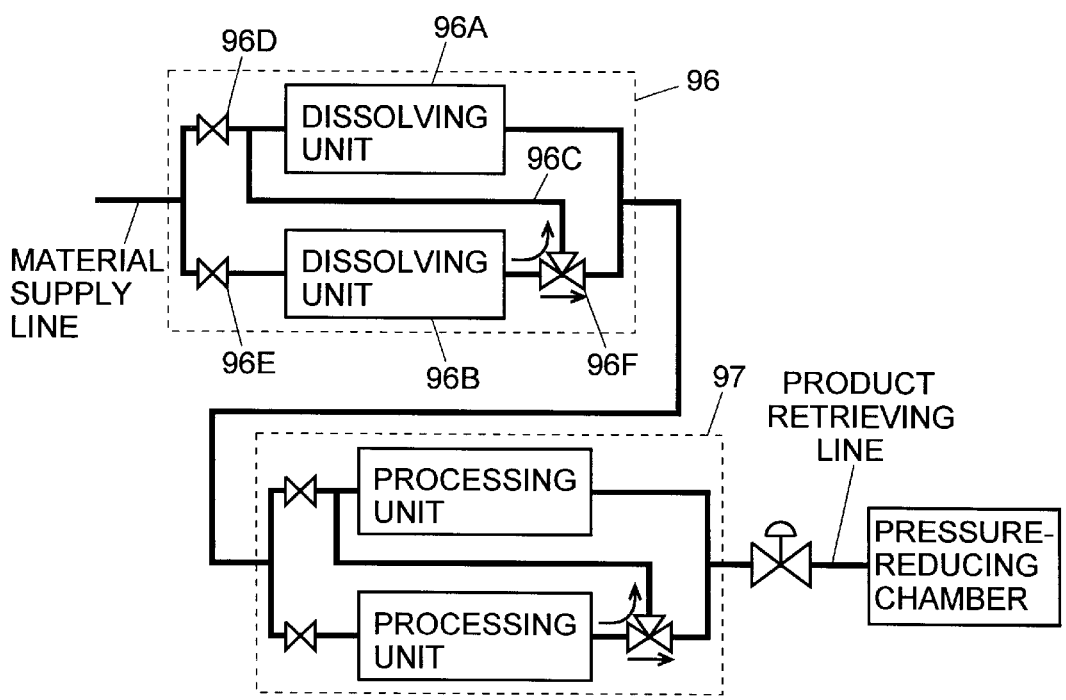

FIGS. 8 and 9 show other examples of the system according to the present invention where a part of the system is constructed using plural units, each of which is independently operative. It should be noted that FIGS. 8 and 9 show only a main part of the system including the dissolving part, the critical processing part and the pressure-reducing part of the invention.

The system shown in FIG. 8 includes two dissolving-and-processing units, each of which includes a dissolving unit 91A and a processing unit 92. The two dissolving-and-processing units are connected in parallel to the material supply pipe and the product retrieving pipe. Either or both of the units can be selected as enabled by appropriately opening or closing valves 94, 94 according to the object of the process.

As for the system shown in FIG. 9, both the dissolving part 96 and the critical processing part 97 are constructed using plural units. The dissolving part 96 is constructed using two dissolving units 96A, 96B, a bypass pipe 96C, two valves 96D, 96E and a three-way valve 96F. By this dissolving part 96, either of the dissolving units 96A, 96B may be selected as enabled, or both of the units 96A, 96B may be connected in series or in parallel by appropriately opening or closing the valves 96D, 96E and changing the direction of the three-way valve 96F according to the object of the process. Similar to the dissolving part 96, the critical processing unit 97 is constructed using two processing units, and the line configuration can be changed similar to the dissolving part 96.

It should be understood that the system of the present invention may be constructed in various forms using plural units other than the above-exemplified constructions.

It should be noted that the above-described embodiments are mere examples and the present invention can be embodied in various forms within its spirit and scope. For example, the dissolution-promoting mechanism, which is constructed using a static mixer in the example of FIG. 6, may be constructed using a mixer having an agitator. As for the formation of micro-particles of liquefied carbon dioxide, an ultrasonic generator may be used in place of the filter. Also, the shape of the warming pipe (20, 62), which is assumed to be spiral in the above embodiments, is not essential to the invention and other shapes may be allowable.

What is claimed is:

1. A method of continuously processing a liquid material with a supercritical or subcritical fluid, comprising:

a) a dissolving stage where a liquefied carbon dioxide is continuously supplied into the liquid material while the liquid material is continuously supplied to dissolve the liquefied carbon dioxide into the liquid material;

b) a critical processing stage where the liquid material with the liquefied carbon dioxide dissolved therein is kept under a preset temperature-and-pressure condition so that the carbon dioxide is brought into a supercritical or subcritical state; and c) a pressure-reducing stage where the pressure of the liquid material after passing the critical processing step is reduced rapidly to remove the carbon dioxide and the liquid material is retrieved as a product.

2. The method according to claim 1, where the dissolving stage includes steps of forming the liquefied carbon dioxide into micro-particles and discharging the micro-particles into the liquid material.

3. The method according to claim 1, where the dissolving stage includes steps of introducing the liquid material and the liquefied carbon dioxide into a dissolving chamber from a bottom of the dissolving chamber and taking out the liquid material from a take-out port provided in an upper part of the dissolving chamber at about a level of the liquid material.

4. A liquid material processed and collected by a method according to claim 1.

5. A system of continuously processing a liquid material with a supercritical or subcritical fluid, comprising:

a) a material supply line for continuously supplying the liquid material:

b) a carbon dioxide supply line for continuously supplying a liquefied carbon dioxide;

c) a dissolving part where the liquefied carbon dioxide supplied through the carbon dioxide supply line is dissolved into the liquid material while the liquid material is continuously supplied through the material supply line;

d) a critical processing part where the liquid material taken out from the dissolving part with the liquefied carbon dioxide dissolved therein is kept under a preset temperature-and-pressure condition so that the carbon dioxide is brought into a supercritical or subcritical state said critical processing part comprising a warming pipe and a heater; and e) a pressure reducing part where a pressure of the liquid material after passing the critical processing part is reduced rapidly for removing the carbon dioxide and the liquid material is collected as a product.

6. The system according to claim 5, where the dissolving part comprises a mechanism for forming the liquefied carbon dioxide into micro-particles and for discharging the micro-particles into the liquid material.

7. A liquid material processed and collected by a system according to claim 5.

8. A system of continuously processing a liquid material with a supercritical or subcritical fluid comprising:

a) a material supply line for continuously supplying the liquid material;

b) a carbon dioxide supply line for continuously supplying a liquefied carbon dioxide;

c) a dissolving part where the liquefied carbon dioxide supplied through the carbon dioxide supply line is dissolved into the liquid material while the liquid material is continuously supplied through the material supply line;

d) a critical processing part where the liquid material taken out from the dissolving part with the liquefied carbon dioxide dissolved therein is kept under a preset temperature-and-pressure condition so that the carbon dioxide is brought into a supercritical or subcritical state; and e) a pressure reducing part where a pressure of the liquid material after passing the critical processing part is reduced rapidly for removing the carbon dioxide and the liquid material is collected as a product,
where the dissolving part is constructed using a material supply pipe constituting the material supply line and the liquefied carbon dioxide from the carbon dioxide supply line is sent into the liquid material flowing in the material supply pipe.

9. A system of continuously processing a liquid material with a supercritical or subcritical fluid, comprising:

a) a material supply line for continuously supplying the liquid material;

b) a carbon dioxide supply line for continuously supplying a liquefied carbon dioxide;

c) a dissolving part where the liquefied carbon dioxide supplied through the carbon dioxide supply line is dissolved into the liquid material while the liquid material is continuously supplied through the material supply line;

d) a critical processing part where the liquid material taken out from the dissolving part with the liquefied carbon dioxide dissolved therein is kept under a preset temperature-and-pressure condition so that the carbon dioxide is brought into a supercritical or subcritical state; and e) a pressure reducing part where a pressure of the liquid material after passing the critical processing part is reduced rapidly for removing the carbon dioxide and the liquid material is collected as a product where the critical processing part includes:

a plurality of processing units operable independent of each other; and a line configuration mechanism for configuring a line or lines in the critical processing part so that the liquid material from the dissolving part is transferred to a part or all of the processing units selected from the plurality of the processing units according to a necessity.

10. The system according to claim 9, further comprising a unit selection part for selecting one, some or all of the plurality of the processing units based on an externally given information relating to a process.

11. A system of continuously processing a liquid material with a supercritical or subcritical fluid comprising:

a) a material supply line for continuously supplying the liquid material;

b) a carbon dioxide supply line for continuously supplying a liquefied carbon dioxide)

c) a dissolving part where the liquefied carbon dioxide supplied through the carbon dioxide supply line is dissolved into the liquid material while the liquid material is continuously supplied through the material supply line;

d) a critical processing part where the liquid material taken out from the dissolving part with the liquefied carbon dioxide dissolved therein is kept under a preset temperature-and-pressure condition so that the carbon dioxide is brought into a supercritical or subcritical state; and e) a pressure reducing part where a pressure of the liquid material after passing the critical processing part is reduced rapidly for removing the carbon dioxide and the liquid material is collected as a product, where the dissolving part includes:

a plurality of dissolving units operable independent of each other; and a line configuration mechanism for configuring a line or lines in the dissolving part so that the liquid material from the material supply line is transferred to a part or all of the dissolving units selected from the plurality of the dissolving units according to a necessity.

12. The system according to claim 11, further comprising a unit selection part for selecting one, some or all of the plurality of the dissolving units based on an externally given information relating to a process.

13. A method of continuously processing a liquid material with a supercritical or subcritical fluid, comprising:

a) a dissolving stage where a liquefied carbon dioxide is continuously supplied into the liquid material while the liquid material is continuously supplied to dissolve the liquefied carbon dioxide into the liquid material;

b) a critical processing stage where the liquid material with the liquefied carbon dioxide dissolved therein is kept under a preset temperature-and-pressure condition so that the carbon dioxide is brought into a supercritical or subcritical state; and c) a pressure-reducing stage where the pressure of the liquid material alter passing the critical processing step is reduced to remove the carbon dioxide and the liquid material is retrieved as a product, where the dissolving stage includes a step of dissolving the liquefied carbon dioxide into the liquid material by sending the liquefied carbon dioxide into the liquid material flowing in a material supply pipe.

14. A system of continuously processing a liquid material with a supercritical or subcritical fluid, comprising:
   a) a material supply line for continuously supplying the liquid material,
   b) a carbon dioxide supply line for continuously supplying a liquefied carbon dioxide;
   c) a dissolving part where the liquefied carbon dioxide supplied through the carbon dioxide supply line-is dissolved into the liquid material while the liquid material is continuously supplied through the material supply line;
   d) a critical processing part where the liquid material taken out from the dissolving part with the liquefied carbon dioxide dissolved therein is kept under a preset temperature-and-pressure condition so that the carbon dioxide is brought into a supercritical or subcritical state; and
   e) a pressure reducing part where a pressure of the liquid material after passing the critical processing part is reduced rapidly for removing the carbon dioxide and the liquid material is collected as a product.
   where the dissolving part includes a dissolving chamber, an inlet for the liquid material from the liquid material supply line and another inlet for the liquefied carbon dioxide from the carbon dioxide supply line are provided at the bottom of the chamber and a take-out port is provided in an upper part of the chamber at about a level of the liquid material.

* * * * *